(12) United States Patent
Valaie

(10) Patent No.: US 8,162,894 B2
(45) Date of Patent: Apr. 24, 2012

(54) VALVE OPENER

(75) Inventor: Arman H. Valaie, Bloomington, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 25 days.

(21) Appl. No.: 12/202,771

(22) Filed: Sep. 2, 2008

(65) Prior Publication Data
US 2008/0319395 A1 Dec. 25, 2008

Related U.S. Application Data

(63) Continuation-in-part of application No. 11/223,333, filed on Sep. 9, 2005.

(51) Int. Cl.
*A61M 5/178* (2006.01)
(52) U.S. Cl. .............................. 604/167.01; 604/167.03
(58) Field of Classification Search .............. 604/167.03
See application file for complete search history.

(56) References Cited

U.S. PATENT DOCUMENTS

| | | | |
|---|---|---|---|
| 2,321,336 A | 6/1943 | Tondreau |
| 2,416,391 A | 2/1947 | Hixson |
| 2,844,351 A | 7/1958 | Smith |
| 3,185,179 A | 5/1965 | Harautuneian |
| 3,304,934 A | 2/1967 | Bautista |
| 3,329,390 A | 7/1967 | Hulsey |
| 3,599,637 A | 8/1971 | Schwartz |
| 3,529,390 A | 9/1971 | Schwartz |
| 4,000,739 A | 1/1977 | Stevens |
| 4,016,879 A | 4/1977 | Mellor |
| 4,063,555 A | 12/1977 | Ulinder |
| 4,243,034 A | 1/1981 | Brandt |
| 4,311,137 A | 1/1982 | Gerard |
| 4,314,555 A | 2/1982 | Sagae |
| 4,424,833 A | 1/1984 | Spector et al. |
| 4,540,411 A | 9/1985 | Bodicky |
| 4,580,573 A | 4/1986 | Quinn |
| 4,610,665 A | 9/1986 | Matsumoto et al. |
| 4,610,674 A | 9/1986 | Suzuki et al. |
| 4,626,245 A | 12/1986 | Weinstein |
| 4,629,450 A | 12/1986 | Suzuki et al. |
| 4,798,594 A | 1/1989 | Hillstead |

(Continued)

FOREIGN PATENT DOCUMENTS

EP 0344907 B1 12/1989

(Continued)

*Primary Examiner* — Nicholas Lucchesi
*Assistant Examiner* — Pritesh Patel
(74) *Attorney, Agent, or Firm* — Brinks Hofer Gilson & Lione

(57) ABSTRACT

A medical introducer apparatus for use in inserting an interventional device into a body vessel of a patient. The apparatus includes a housing having a proximal opening, a distal opening, and a chamber positioned between the openings. A hemostatic valve system is provided in the housing chamber. The valve system includes a plurality of generally elastomeric valve members axially arranged in the chamber. The valve members each have a generally circular hole extending therethrough, which hole is sized for substantially leak-free passage of the interventional device. The valve members are aligned in the chamber to be sequentially penetrable by the interventional device, such that a hole in one valve member is covered by an adjoining valve member. A valve opener having a tubular body with a curved portion penetrates the hemostatic valve system to aid in the positioning of the interventional device. The curved portion maintains the valve opener stationary within the valve system.

19 Claims, 7 Drawing Sheets

U.S. PATENT DOCUMENTS

| | | | |
|---|---|---|---|
| 4,895,565 A | 1/1990 | Hillstead |
| 4,929,235 A | 5/1990 | Merry et al. |
| 4,932,633 A | 6/1990 | Johnson et al. |
| 4,978,341 A | 12/1990 | Niederhauser |
| 5,000,745 A | 3/1991 | Guest et al. |
| 5,006,113 A | 4/1991 | FischeSteigerwaldr |
| 5,009,391 A | 4/1991 | Steigerwald |
| 5,053,013 A | 10/1991 | Ensminger et al. |
| 5,062,836 A | 11/1991 | Wendell |
| 5,066,285 A | 11/1991 | Hillstead |
| 5,098,393 A | 3/1992 | Amplatz et al. |
| 5,102,395 A | 4/1992 | Cheer et al. |
| 5,125,903 A | 6/1992 | McLaughlin et al. |
| 5,154,701 A | 10/1992 | Cheer et al. |
| 5,158,553 A | 10/1992 | Berry et al. |
| 5,167,637 A | 12/1992 | Okada et al. |
| 5,176,652 A | 1/1993 | Littrell |
| 5,211,370 A | 5/1993 | Powers |
| 5,242,413 A | 9/1993 | Heiliger |
| 5,256,150 A | 10/1993 | Quiachon et al. |
| 5,267,966 A | 12/1993 | Paul |
| 5,304,156 A | 4/1994 | Sylvanowicz et al. |
| 5,350,363 A | 9/1994 | Goode et al. |
| 5,350,364 A | 9/1994 | Stephens et al. |
| 5,376,077 A | 12/1994 | Gomringer |
| 5,385,552 A | 1/1995 | Haber et al. |
| 5,395,349 A | 3/1995 | Quiachon et al. |
| 5,395,352 A | 3/1995 | Penny |
| 5,409,463 A | 4/1995 | Thomas et al. |
| 5,429,616 A | 7/1995 | Schaffer |
| 5,484,418 A | 1/1996 | Quiachon et al. |
| 5,538,505 A | 7/1996 | Weinstein et al. |
| 5,554,117 A | 9/1996 | Ensminger et al. |
| 5,613,956 A | 3/1997 | Patterson et al. |
| 5,643,227 A | 7/1997 | Stevens |
| 5,653,697 A | 8/1997 | Quiachon et al. |
| 5,702,370 A | 12/1997 | Sylvanowicz et al. |
| 5,779,681 A | 7/1998 | Bonn |
| 5,895,376 A | 4/1999 | Schwartz et al. |
| 5,908,409 A | 6/1999 | Rinehart et al. |
| 5,911,710 A | 6/1999 | Barry et al. |
| 5,935,122 A | 8/1999 | Fourkas et al. |
| 6,086,570 A | 7/2000 | Aboul-Hosn et al. |
| 6,170,800 B1 | 1/2001 | Meloul et al. |
| 6,197,016 B1 | 3/2001 | Fourkas et al. |
| 6,221,057 B1 | 4/2001 | Schwartz et al. |
| 6,287,280 B1 | 9/2001 | Lampropoulos et al. |
| 6,416,499 B2 | 7/2002 | Paul, Jr. |
| 6,541,802 B2 | 4/2003 | Doyle |
| 6,562,049 B1 | 5/2003 | Norlander et al. |
| 6,585,697 B2 | 7/2003 | Kempen et al. |
| 6,610,031 B1 * | 8/2003 | Chin .................. 604/167.04 |
| 6,981,966 B2 | 1/2006 | Green et al. |
| 7,008,404 B2 | 3/2006 | Nakajima |
| 7,147,621 B2 | 12/2006 | Kiehne |
| 2003/0144670 A1 | 7/2003 | Pavcnik et al. |
| 2003/0216771 A1 | 11/2003 | Osypka et al. |
| 2004/0106942 A1 * | 6/2004 | Taylor et al. .................. 606/185 |
| 2004/0230161 A1 | 11/2004 | Zeiner |
| 2005/0096605 A1 | 5/2005 | Green et al. |
| 2005/0159710 A1 | 7/2005 | Utterberg |
| 2005/0171479 A1 | 8/2005 | Hruska et al. |
| 2005/0182476 A1 | 8/2005 | Hartley et al. |
| 2005/0187524 A1 | 8/2005 | Willis et al. |
| 2006/0135977 A1 | 6/2006 | Thompson et al. |
| 2006/0229564 A1 | 10/2006 | Andersen et al. |
| 2007/0073242 A1 | 3/2007 | Andersen et al. |
| 2007/0078395 A1 | 4/2007 | Valaie |
| 2007/0219614 A1 | 9/2007 | Hartley |
| 2008/0108944 A1 | 5/2008 | Woehr et al. |

FOREIGN PATENT DOCUMENTS

| | | |
|---|---|---|
| EP | 0550069 A1 | 7/1993 |
| EP | 0755694 A1 | 1/1997 |
| EP | 1374942 A1 | 1/2004 |
| WO | 0035209 | 6/1999 |

* cited by examiner

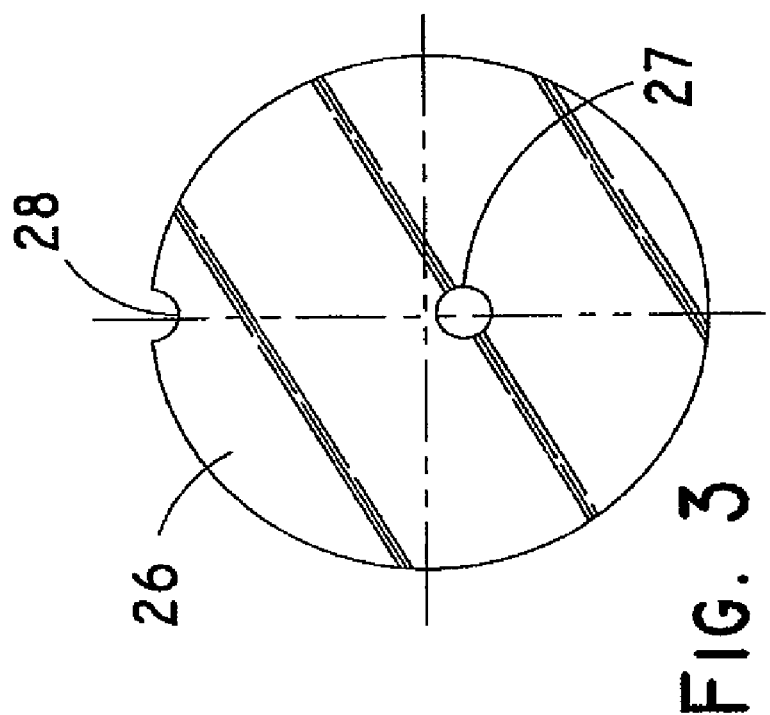
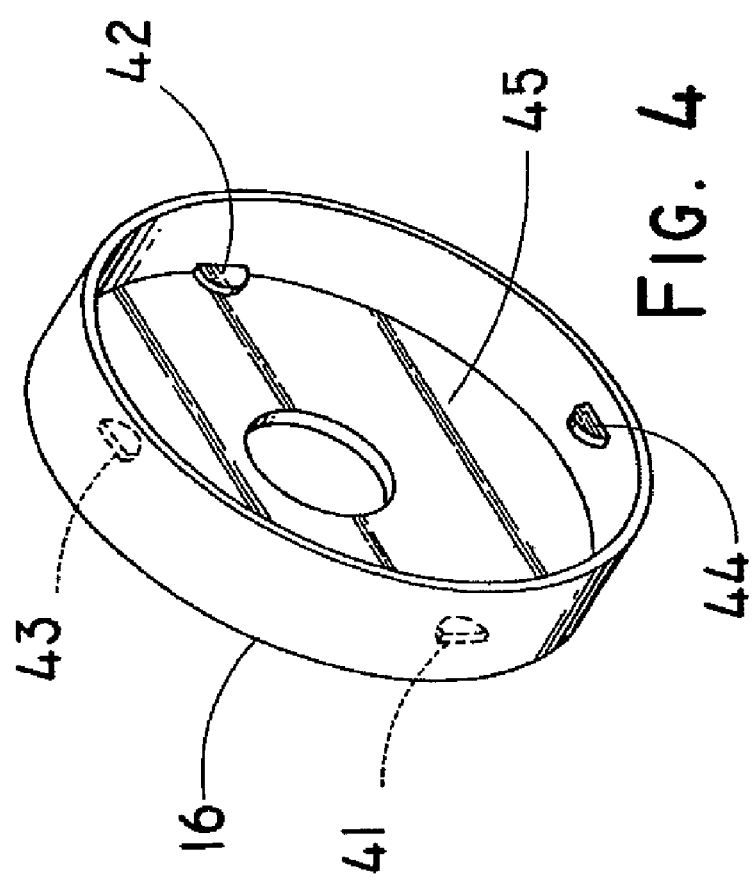

VALVE OPENER

CROSS-REFERENCE TO RELATED APPLICATIONS

This application is a continuation-in-part of copending U.S. patent application Ser. No. 11/223,333, filed Sep. 9, 2005, which is incorporated by reference herein in its entirety.

BACKGROUND

1. Field of the Invention

The present invention relates to a valve system for use with a medical device and a valve opener for use with a valve system. More particularly, the invention relates to a medical device, such as an introducer, having a hemostatic valve system that allows substantially leak-free passage of a medical interventional device through the medical device for insertion into a body vessel and a substantially stationary valve opener which allows the passage of a medical interventional device, such as a wire guide, through the medical device for insertion into a body vessel.

2. Background Information

Numerous procedures have been developed in modern medicine that require the percutaneous insertion of one or more medical interventional devices into the vascular system. Such procedures include, for example, percutaneous transluminal coronary angioplasty (PTCA), X-ray angiographic procedures, and the like.

The medical interventional devices intended for use in such procedures may be introduced into the vascular system by a variety of known techniques. One widely-used technique is the Seldinger technique. In the Seldinger technique, a surgical opening is made in an artery or vein by a needle, and a wire guide is inserted into the artery or vein through a bore in the needle. The needle is thereafter withdrawn, leaving the wire guide in place. A dilator which is positioned within the lumen of an introducer device is then inserted over the wire guide into the artery or vein. Once the introducer is properly positioned within the artery or vein, the dilator is withdrawn. The introducer may then be utilized in conventional fashion for the insertion therethrough of a variety of types of medical devices, such as catheters, cardiac leads, and the like.

In many cases, an introducer will include one or more hemostatic valve members (also referred to as check valves) for inhibiting leakage of bodily fluids, such as blood, back through the introducer as a medical interventional device is inserted or withdrawn therethrough. The valve members are generally positioned in a housing of the introducer, between a main body portion and an end cap. Typically, such valve members comprise one or more elastomeric disks having one or more slits extending through all or a portion of the disk. On some occasions the valve members may comprise at least one disk having one or more slits, and at least one additional disk having a hole extending through the center of the disk. The slits and/or holes are sized to enable the medical interventional device to pass through the valve member, and to substantially prevent the backflow of fluids through the valve. Hemostatic valves are well known in the medical arts for such purpose, and no further general discussion of the use and function of such valves is necessary to an understanding of the present invention.

Frequently, it is necessary to replace a previously-inserted medical interventional device with another interventional device of a different diameter, or with a different type of device. Such exchanges are normally made over a wire guide, wherein the old device is withdrawn over the wire guide, and the new device is thereafter inserted into the vasculature over the existing wire guide or a newly-inserted wire guide. In many such cases, elastomeric hemostatic valves are provided in an attempt to minimize leakage of blood back through the introducer. Such valves are dependent upon the elasticity of the valve body, and its ability to draw back upon itself to seal any gap created upon insertion or withdrawal of a device through the valve.

Known slitted hemostatic valves generally include one or more slits that criss-cross and span a center portion of the valve, or a hole disposed through the center of the disk. As the interventional device is passed through the center of a slit valve, the slits open outwardly and form one or more generally "V"-shaped openings that are disposed along the outer surface of the interventional device. Such linear-type openings do not form tight seals, and inherently create gaps that permit the leakage of at least some fluid. As a result, hemostatic valve systems often comprise two or three such valve members that are aligned in the valve housing in a manner such that the slit portions are not in axial alignment. Although this arrangement may reduce the amount of leakage compared to the use of a single valve member, the presence of the gaps continues to provide a conduit from which some leakage may occur. Similarly, the various flaps resulting from the slits do not always re-set in the proper manner following passage of the interventional device, thereby creating additional gaps through which fluid may leak.

In addition to the foregoing, when larger slitted valves are utilized, the interventional devices may tear the valve disk beyond the slits upon insertion. This is particularly true when larger size interventional devices are inserted. In such cases, multiple valve disks must be incorporated in order to provide a reasonable degree of confidence that the valve system will continue to provide at least some leakage control. In some cases, the damage to the valve may be so severe, that it may be necessary to incorporate another type of valve, such as a Tuohy-Borst type valve, to the introducer.

Similarly, when smaller slitted valves are utilized, the valves are also subject to tearing when smaller size interventional devices are passed therethrough. Small size interventional devices are often delicate, and possess little hoop strength. When such devices are passed through a small valve member, the thickness and strength of the valve member may cause damage to the delicate structure upon passage therethrough of the interventional device. When small disks are used, the clearance between the opening in the disk and the interventional device can be so slight that it may be difficult to insert and/or withdraw the interventional device. In addition, on some occasions, additional small diameter tubing must be used to keep the valve open so that a catheter may be passed therethrough. When additional equipment is required, such as a small diameter tube or a Tuohy-Borst valve as described, the surgeon's hands, and attention, may be unduly distracted at the very time when all possible focus should be on the major task at hand.

When one or more disks having a hole through the center are used, the disks will only retract back to the size of the center hole following removal of the catheter. As a result, the respective center holes allow leakage once the catheter is removed. Such valves may be satisfactory when there is no need to remove the catheter that seals the opening, however, they are problematic when the catheter is removed and the center opening is created.

Valve disks are likely lubricated with silicon and catheters or wire guides are likely coated with some sort of hydrophilic coating which may collect and coat the valve disks. Thus, traditional valve openers having a generally uniform diameter have a tendency to pop out from the valve system due to the lubrication coating or due to the blood within the valve system.

Therefore, it is desired to provide a hemostatic valve system for a medical device that provides an effective seal, and that avoids the problems encountered with prior art seals and it is further desired to provide an improved valve opener for a hemostatic valve system that will have a reduced risk of popping out from within the valve system during insertion and withdrawal of wire guides.

BRIEF SUMMARY OF THE INVENTION

The problems of the prior art are addressed by the present invention. In one form thereof, the invention comprises a valve opener for insertion through a valve system having a plurality of axially arranged valve members. Each valve member includes a generally circular hole extending therethrough. The valve opener includes a tubular body having proximal and distal ends and a central bore formed therethrough defining a longitudinal axis. The tubular body includes a handle portion extending from the proximal end to a larger diameter portion and a distal portion extending from the larger diameter portion to the distal end. The distal portion includes a curved portion defined by a flared section extending from the larger diameter section and a tapered section extending from the flared section. The larger diameter portion is greater in diameter than the largest diameter of the distal portion. The flared section has an increasing outer diameter distally along the longitudinal axis and the tapered section has a decreasing outer diameter distally along the longitudinal axis to the distal end.

In another form thereof, the invention comprises a hemostatic valve system for use in a medical introducer. The valve system comprises a plurality of valve members axially arranged in the medical introducer, and having a hole extending therethrough. The holes have a diameter that does not substantially exceed a diameter of an interventional device to be passed through the medical introducer and the valve members. The valve members are aligned in the medical introducer such that the holes are penetrable by the interventional device, and such that a hole in one valve member is covered by an adjoining valve member.

In this embodiment, a valve opener is configured to advance through the plurality of valve members to establish a pathway through the valve members for insertion of the interventional device. The valve opener includes a tubular body having proximal and distal ends and a central bore formed therethrough defining a longitudinal axis. The tubular body includes a handle portion extending from the proximal end to a larger diameter portion and a distal portion extending from the larger diameter portion to the distal end. The distal portion includes a curved portion defined by a flared section extending from the larger diameter section and a tapered section extending from the flared section. The larger diameter portion is greater in diameter than the largest diameter of the distal portion. The flared section has an increasing outer diameter distally along the longitudinal axis and the tapered section has a decreasing outer diameter distally along the longitudinal axis to the distal end.

In still another form thereof, the invention comprises a method of introducing an interventional device to a target site in the vasculature of a patient. A valve opener is inserted through a proximal end of an introducer for use in inserting the interventional device. The introducer comprises a housing surrounding a chamber and a valve system disposed within the chamber. The valve system includes a plurality of valve members axially arranged in the chamber. Each valve member has a generally circular hole extending therethrough, which hole is sized for passage of the interventional device. The valve members are aligned in the chamber such that each of the holes is penetrable by the interventional device, and such that a hole in one valve member is covered by an adjoining valve member.

In this method, the valve opener includes a tubular body having proximal and distal ends and a central bore formed through the proximal and distal ends defining a longitudinal axis. The tubular body includes a handle portion extending from the proximal end to a larger diameter portion and a distal portion extending from the larger diameter portion to the distal end. The distal portion includes a curved portion defined by a flared section extending from the larger diameter section and a tapered section extending from the flared section. The larger diameter portion is greater in diameter than the largest diameter of the distal portion. The flared section has an increasing outer diameter distally along the longitudinal axis and the tapered section has a decreasing outer diameter distally along the longitudinal axis to the distal end. The valve opener is advanced through the introducer in a manner such that the valve opener sequentially penetrates each of the circular holes thereby establishing a path for the interventional device, wherein the larger diameter portion acts as a stop to prevent further insertion of the valve opener within the introducer. A wire guide is advanced through the central bore of the valve opener such that the wire guide extends through the introducer, and a distal end of the wire guide extends beyond a distal end of the introducer, wherein the curved section of the valve opener keeps the valve opener stationary within the introducer during insertion of the wire guide.

BRIEF DESCRIPTION OF THE DRAWINGS

FIG. 3 is a front view of one example of an elastomeric valve disk for use in the present invention;

FIG. 4 is a perspective view of an end cap for the apparatus;

DETAILED DESCRIPTION

Figure 1:
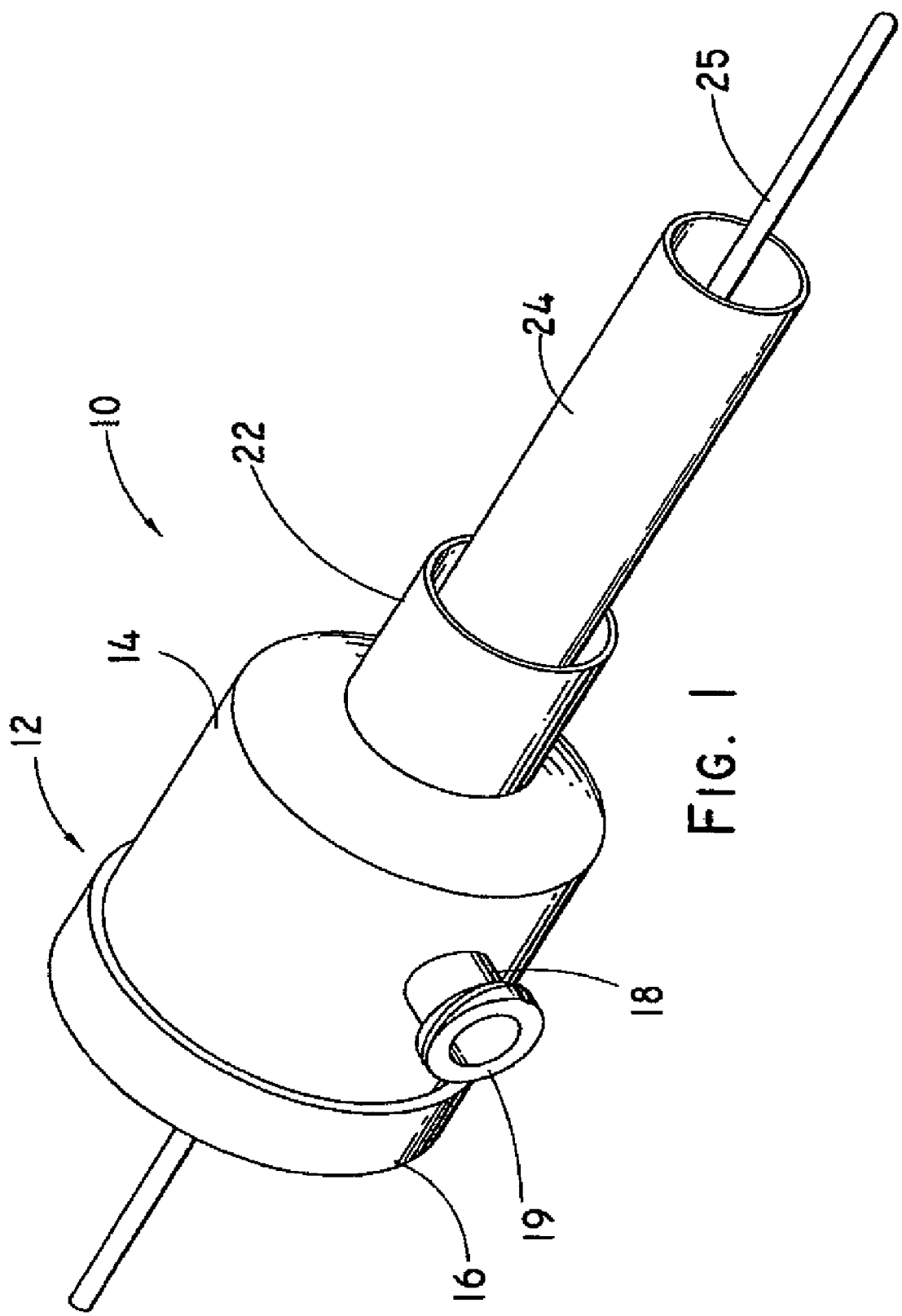
FIG. 1 is a perspective view of one embodiment of a medical introducer apparatus according to the present invention.

For purposes of promoting an understanding of the present invention, reference will now be made to the embodiments illustrated in the drawings, and specific language will be used to describe the same. It is nevertheless to be understood that no limitation of the scope of the invention is thereby intended, the proper scope of the invention being indicated by the claims appended below and the equivalents thereof. The figures are not all drawn to the same scale to avoid obscuring the details of the finer structures. The following detailed description of the preferred embodiments will make clear the preferred arrangement, size relationships and manner of using the components shown herein.

The present invention relates to a medical introducer apparatus, to a hemostatic valve system that may be utilized in such an apparatus, and to a valve opener that may be utilized in such a valve system. In the following discussion, the terms "proximal" and "distal" will be used to describe the opposing axial ends of the apparatus, as well as the axial ends of the valve members and other component features. The term "proximal" is used in its conventional sense to refer to the end of the introducer apparatus (or component thereof) that is closer to the operator during use of the device. The term "distal" is used in its conventional sense to refer to the end of the introducer apparatus (or component thereof) that is initially inserted into the patient, or that is closer to the patient.

Figure 2:
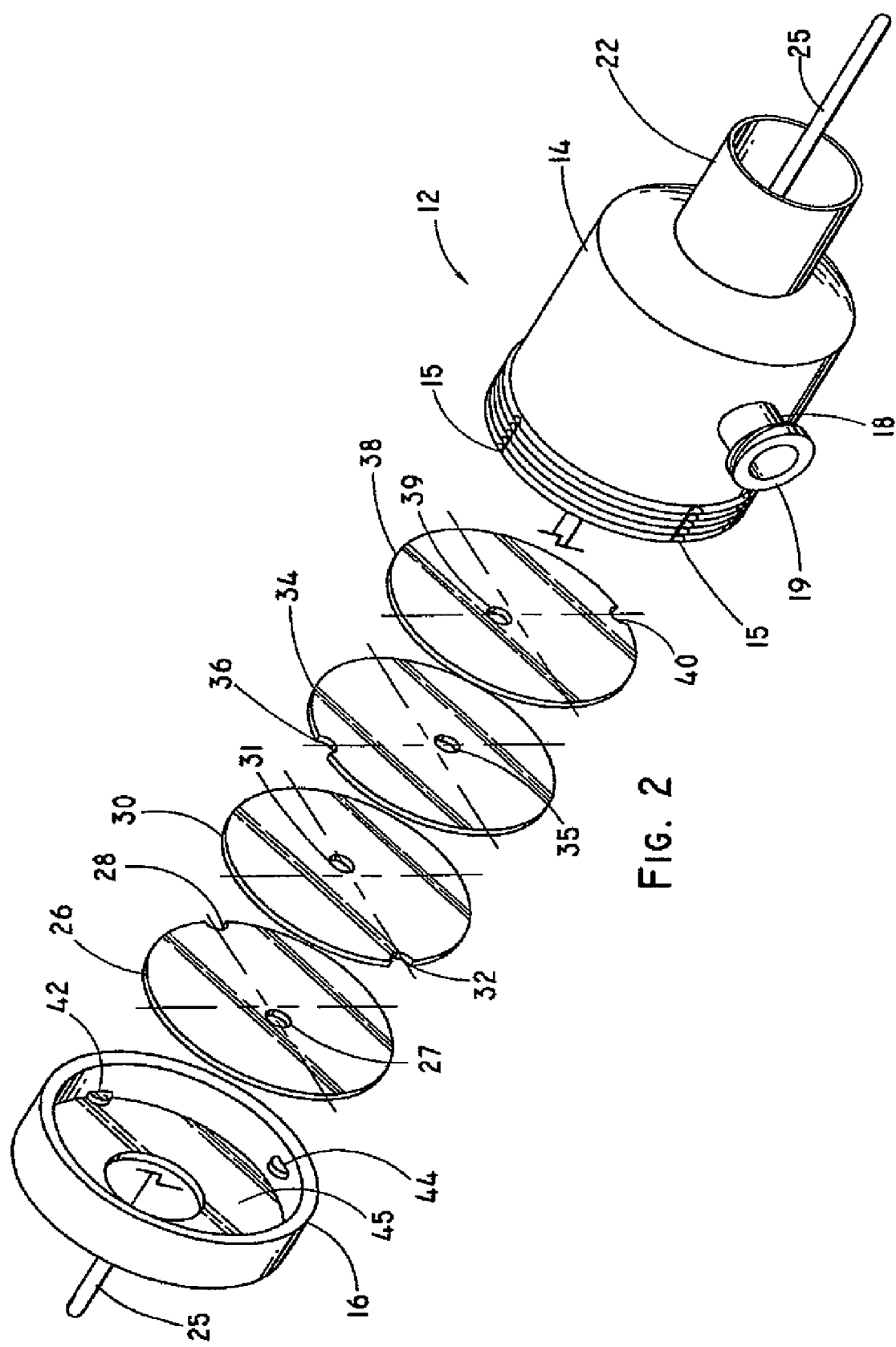
FIG. 2 is an exploded view of a proximal portion of the introducer apparatus of FIG. 1.

FIG. 1 illustrates a perspective view of one embodiment of a medical introducer apparatus 10 according to the present invention. The features of introducer apparatus 10 visible in FIG. 1 are conventional, and are common in many commercially available introducers. FIG. 2 illustrates an exploded view of introducer apparatus 10. The exploded view illustrates one non-limiting example of an inventive valve system for use in the introducer apparatus.

The embodiment of introducer apparatus 10 illustrated herein includes a housing 12, wherein the housing comprises main body 14 and end cap 16. Main body 14 and end cap 16 may be joined in any conventional fashion, such as by a screw fit or a snap fit. In the embodiment shown in FIG. 2, main housing body 14 has one or more screw threads that correspond with a lip or other suitable structure in the end cap. Body 14 also includes a plurality of grooves 15 that generally correspond to tabs in the end cap, as discussed hereafter. Housing 12 may also include a side-arm spout 18 extending in a generally transverse direction from main housing body 14. Preferably, spout 18 includes a lip 19 sized and shaped for threaded or like engagement with a tube or other device (not shown), for use in the transmittal or aspiration of a fluid or a drug in conventional fashion. The distal end of main housing body 14 comprises a smaller diameter portion 22. A removable sheath 24 extends distally from smaller diameter portion 22 of housing 12 in conventional fashion. In the embodiment shown, a wire guide 25 is shown extending through apparatus 10.

The exploded view of FIG. 2 illustrates main housing body 14, end cap 16, and elastomeric valve disks 26, 30, 34, 38 axially aligned between main body 14 and end cap 16. The use of elastomeric disks as hemostatic (check flow) valves is well known in the medical industry. The disks used herein have sufficient elasticity to enable an opening formed therein to stretch to the extent required to allow an interventional device to pass therethrough, and to substantially return to a pre-stretched condition following relaxation of the force generated upon insertion of the device. The disks can be formed to have any desired diameter and thickness, depending upon the size of the interventional device, and the desired pressure rating of the valve system. The disks used herein are preferably formed from elastomeric materials such as silicone or urethane, although any suitable composition known in the art for such purposes may be substituted.

In the preferred embodiment of FIG. 2, each disk has a generally circular hole extending therethrough, which hole is sized to enable passage of the interventional device. Preferably, the hole is capable of being stretched during insertion of an interventional device having a larger diameter than the diameter of the hole, such that there is little or no clearance between the hole and the device so that a tight seal is formed therebetween.

Disk 26 is shown in FIG. 3 removed from the inventive apparatus to better illustrate features of the disks. Hole 27 is punched or otherwise formed through disk 26. As shown, hole 27 is offset from the radial center of the disk (shown as the intersection of the two axes present as broken lines). The distance of the offset from the center portion of the disk may be selected according to the desired pressure rating for the valve. Preferably, a keyed portion, such as notch 28, is provided along the outer circumference of disk 26, for reasons to be discussed.

In the preferred embodiment shown, apparatus 10 includes multiple disks that are each configured in the same manner as disk 26. As best illustrated in the exploded view of FIG. 2, each disk 26, 30, 34, 38 includes a respective hole 27, 31, 35, 39, and a respective notched portion 28, 32, 36, 40. The holes are offset from the center portion in the manner best shown in FIG. 3. Preferably, the holes are offset in the portion of the disk directly opposite the notched portion.

The disks and the housing are preferably provided with cooperating structure that maintains the respective disks in a particular orientation within apparatus 10. In the preferred embodiment shown, the disks are each provided with a shaped portion, such as the notched portion 28 shown in FIG. 3. When the apparatus is fully assembled, the shaped portion of the disk cooperates with a corresponding shaped portion, such as a tab, that is provided in the end cap. The shaped portion of the disk and the corresponding shaped portion of the end cap cooperate in the nature of a keyed structure, to maintain the disk in a desired orientation within the housing. FIG. 4 illustrates one possible arrangement of keyed tabs that may be provided on housing end cap 16. In the embodiment shown, housing end cap 16 includes four tabs 41, 42, 43, 44. Tab 42 is the deepest tab in housing end cap 16. When the apparatus is fully assembled, tab 42 corresponds with notch 28 of disk 26, to hold that disk in the preferred rotational orientation. Disk 26 thus essentially rests on floor portion 45 of housing end cap 16. This may also be visualized from the view of FIG. 2. Similarly, tab 41 corresponds with notch 32 of disk 30, tab 43 corresponds with notch 36 of disk 34, and tab 44 corresponds with notch 40 of disk 38. It should be noted that each of the tabs is positioned at a different depth in end cap 16. This depth corresponds to the positioning of the various disks as they are stacked in the housing, and to the position of the notch that corresponds to the respective tab. Each of the tabs thus retains a specified disk in a particular orientation in the housing.

Figure 5:
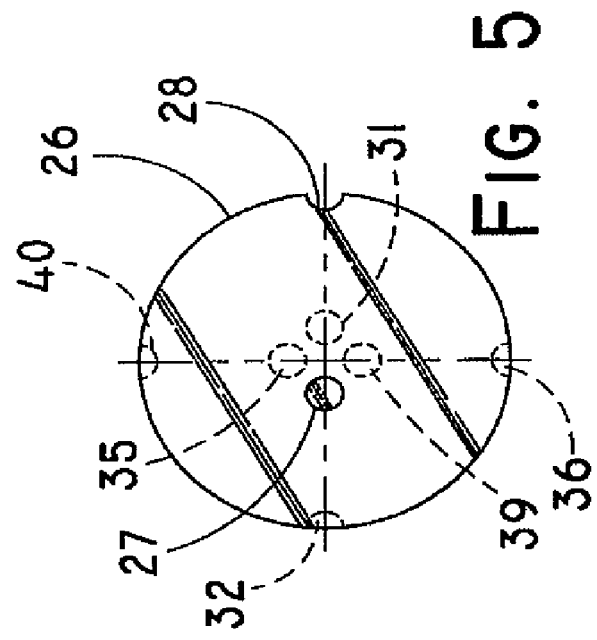
FIG. 5 is a view of one embodiment of a 4-disk valve system of the present invention taken from a proximal perspective.

When the introducer apparatus includes four disks, the disks are preferably aligned as shown in FIG. 2. In this case, disks 26 and 30 are rotated approximately 180 degrees from each other, such that respective notches 28, 32 are disposed 180 degrees apart in the assembled device. Similarly, disks 34 and 38 are rotated so that notches 36, 40 are disposed approximately 180 degrees from each other. Thus, in the finished device, each one of holes 27, 31, 35, 39 is disposed in a separate quadrant of the valve system as shown. Stated another way, in the completed apparatus, there is a hole at 90, 180, 270 and 360 degrees, relative to a designated starting point. This is shown in the disk alignment of FIG. 2, and may also be visualized by the end view of FIG. 5. FIG. 5 comprises the alignment of the disks as they are stacked in the housing, when viewed from a vantage point proximal of disk 26. The features of disk 26, such as hole 27 and notched portion 28, are illustrated in solid lines, since these features are visible in this view. Features of the remaining disks 30, 34, 38, which are successively aligned behind disk 26, are shown in broken lines to indicate the relative positioning of these features relative to the features of disk 26 in the assembled apparatus. As stated, these additional features are not directly visible in the view of FIG. 5 since they are positioned behind disk 26 when viewed from this perspective.

Although FIGS. 2 and 5 illustrate the presence of four disks, the valve system need not include exactly four disks. Thus, more, or fewer, disks may be utilized in a particular case. For example, when the apparatus includes two disks, the disks are preferably aligned such that each disk is rotated about 180 degrees from the other disk. As a result, each one of holes is disposed in a separate circumferential half of the valve system. Similarly, when a valve system includes three disks, the disks may be aligned such that each disk is rotated about 120 degrees from the immediately preceding disk, and each hole is disposed in a separate circumferential third of the valve system. Those skilled in the art will appreciate that other numbers of disks may be used, in which case the disks may be aligned in a corresponding manner.

It is an important feature of the invention to align the disks such that the holes in immediately adjacent disks are not substantially overlapping, and preferably, do not overlap at all. This alignment may be best visualized in FIG. 5. In this arrangement, it is observed that the holes do not overlap when the disks are assembled in the inventive apparatus. Although it is preferred that the holes not overlap, a small amount of overlap may be acceptable in certain instances. Similarly, it is preferred to align the disks such that the holes are equally spaced along the circumference of a valve system, as shown in the embodiment of FIG. 5. However, this is not necessarily required in all instances, as long as the holes in immediately adjacent disks are not substantially overlapping. Nonetheless, it is preferred to align the disks such that the holes are substantially equally spaced, as it is believed that a better seal is provided.

In general, an introducer apparatus having a valve system that includes a large number of valve disks has an increased overall pressure rating when compared to a valve system having a smaller number of disks. For example, the valve system shown in FIGS. 2 and 5 comprising four valves would have a higher overall pressure rating than a valve system having two or three valves, other factors being equal. Similarly, a valve system having disks in which the holes are further away from the radial center of the disk will have a higher pressure rating than a valve system wherein the holes are at or near the radial center of the disk.

Thus, in applications in which valves having a high pressure rating are desired, a valve system having a high number of valve disks (such as four), and/or a valve system wherein the holes in the valve disks are spaced from the center of the disk is preferred. On the other hand, when a low pressure valve system is acceptable, a valve system having a lower number of valve disks (such as two), and/or a valve system wherein the holes in the valve disks are closer to the radial center of the disk may be satisfactory. When utilizing the teachings provided herein, those skilled in the art can readily select a valve arrangement having a desired number of disks, and an appropriate spacing of the hole from the center of the disk, to obtain an appropriate pressure rating for a particular application without undue experimentation.

Figure 13:
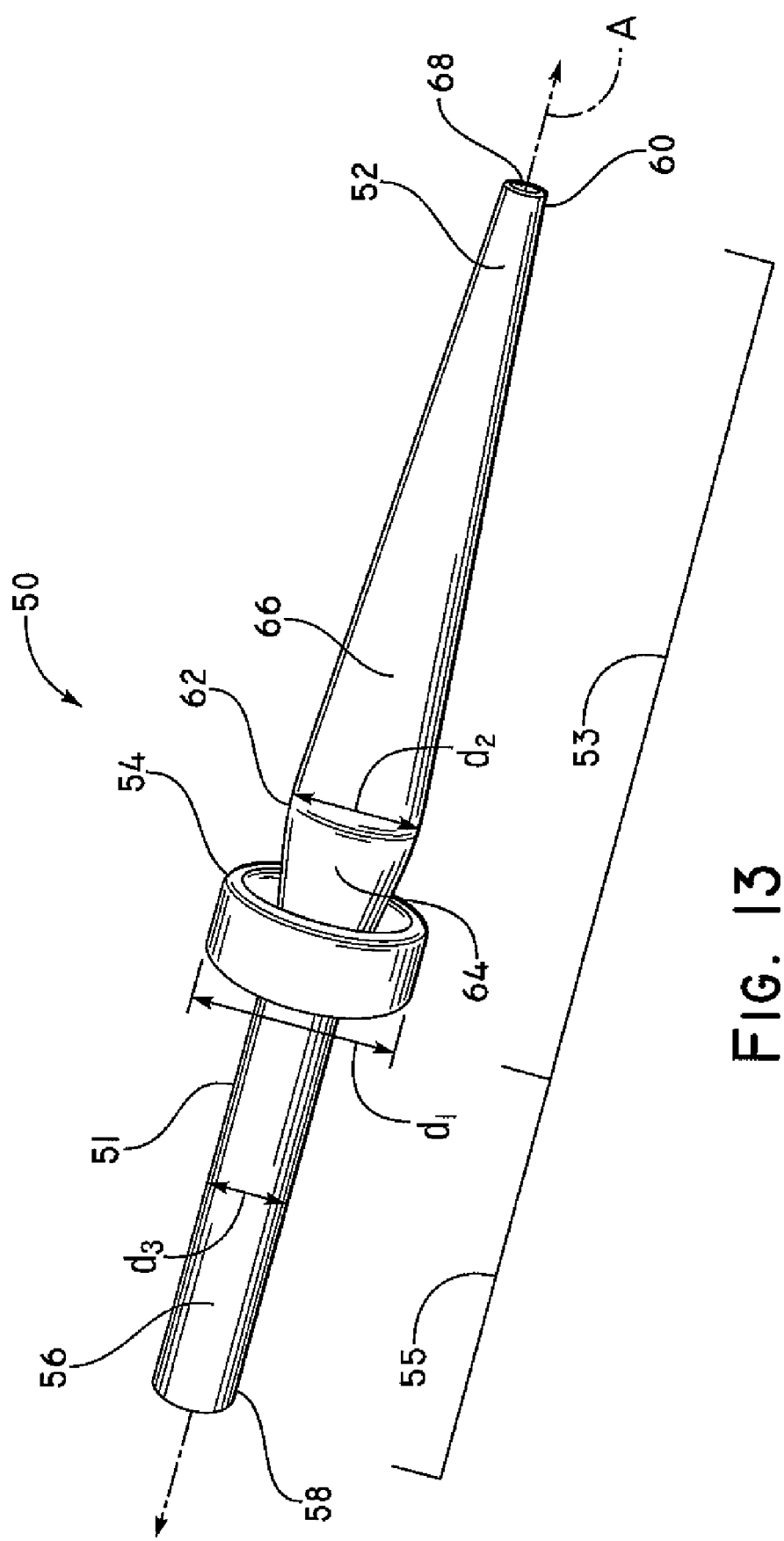
FIG. 13 is a perspective view of an opener in accordance with an embodiment of the present invention, with the larger diameter portion formed integrally with the tubular body of the valve opener.
Figure 14:
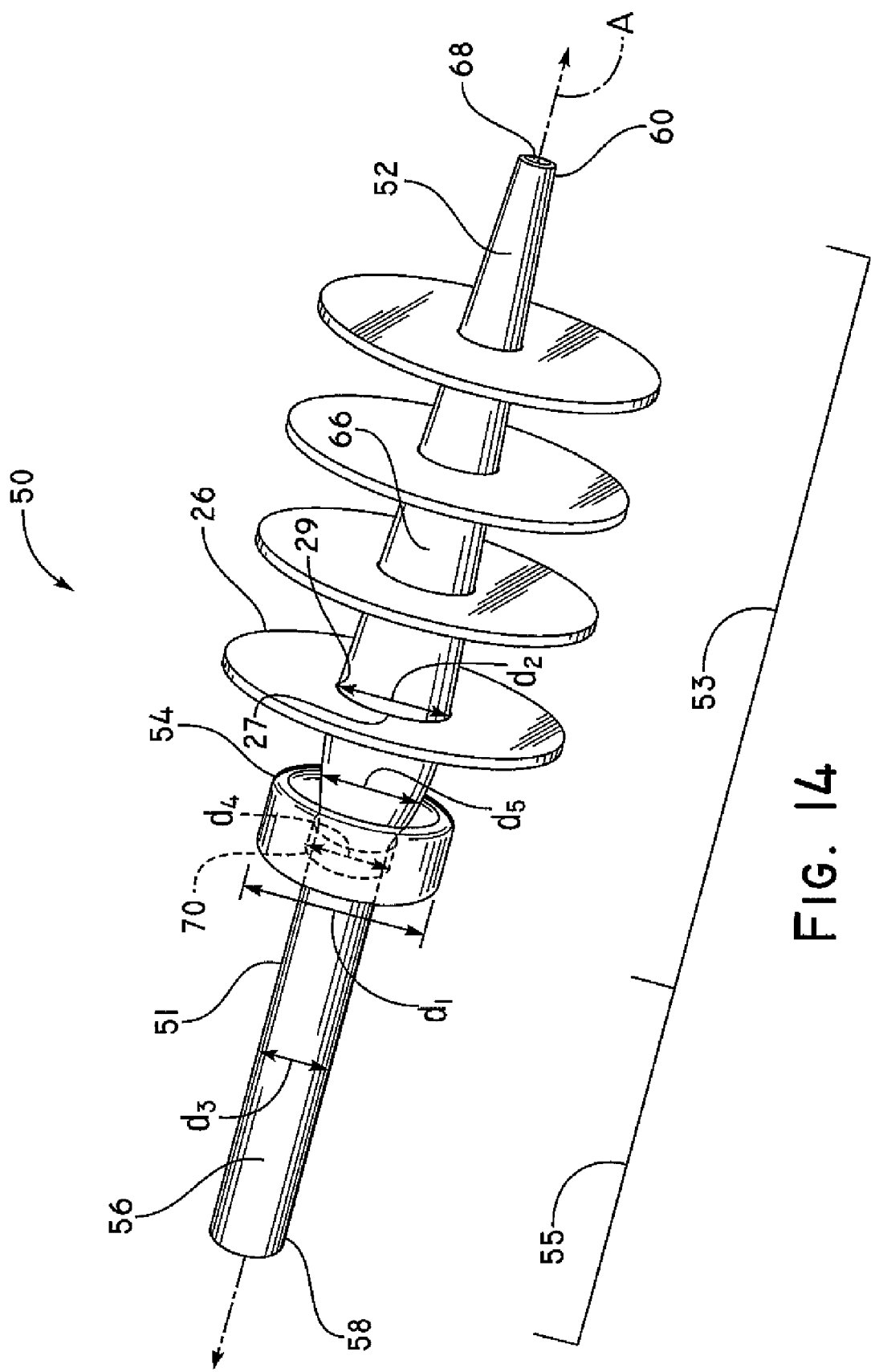
FIG. 14 is a perspective view of an opener penetrating the holes of the valve disks in accordance with an embodiment of the present invention, with the larger diameter portion formed as a separate member from the tubular body of the valve opener.

An opener 50 is used to initially establish a pathway through the valves of introducer apparatus 10. Referring to FIGS. 13-14, the opener 50 is provided with a tubular body 51 having a distal portion 53 and a proximal portion 55. The proximal portion 55 includes a handle 56 which extends from the proximal end 58 to a larger diameter portion 54. The distal portion 53 extends from the larger diameter portion 54 to the distal end 60 and includes a curved portion 62 defined by a flared section 64 extending from the larger diameter portion 54 and a tapered section 66 extending from the flared section 64 to a narrow tip portion 52. A central bore 68 is formed through the proximal and distal ends 58, 60 defining a longitudinal axis A.

In this embodiment, the larger diameter portion 54 has a first outer diameter d1 greater than the largest outer diameter d2 of the distal portion 53. The diameter of the flared section 64 gradually continuously increases distally along the longitudinal axis A defining an inclined portion such that the diameter of the flared section 64 becomes successively larger from the point at which the flared section 64 meets the larger diameter potion 54 to the point at which the flared section 64 meets the tapered section 66. The diameter of the tapered section 66 gradually continuously decreases distally along the longitudinal axis A defining a declined portion from the flared section 64 to the distal end such that the diameter of the tapered section 66 becomes successively smaller from the point at which the tapered section 66 meets the flared section 64 to the distal end 60.

Figure 6:
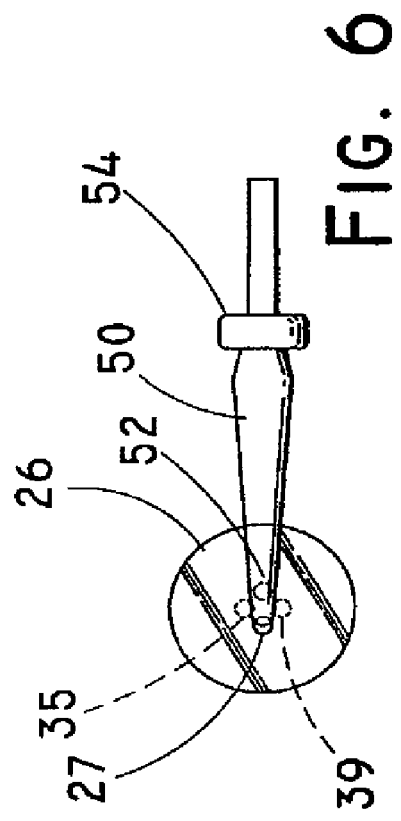
FIG. 6 shows an opener in accordance with an embodiment of the present invention penetrating the hole in the first disk.

FIG. 6 schematically illustrates the arrangement of the disks as disk 26 is initially penetrated by opener 50. FIG. 14 shows the opener penetrating through the valve disks 26, 30, 34, 38. As illustrated in FIG. 6, the narrow tip portion 52 is directed in the apparatus 10 such that it initially passes through hole 27 of disk 26. Tip portion 52 is then successively directed through holes 31, 35, 39 of respective disks 30, 34, 38, until it passes through each of the disk valves.

Figure 7:
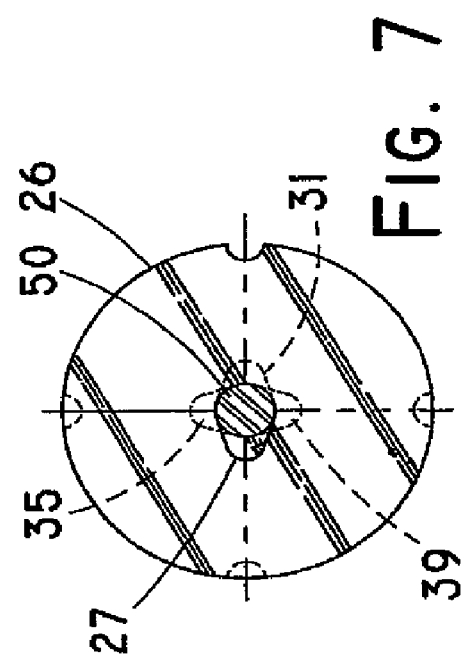
FIG. 7 illustrates the arrangement of disks shown in FIG. 5, following penetration of all four disks by the opener, showing the stretching of the disks toward the radial center of the disk.

Typically, as the opener 50 passes through the successive valve disks, it finds the radially inner edge of each successive hole, at which time the opener 50 can be manipulated to stretch the hole in an up and down, and in a side to side motion. As the tip portion 52 passes through the successive disks, the holes stretch toward the center of the disk. The opener 50 is continually advanced until it reaches the radial inner edge of the next hole, and the stretching process is repeated. This process is continued until the opener 50 has penetrated the hole in each of the successive disks. Once tip portion 52 has passed through all four of the disk holes, the holes are each stretched from the original "rounded" configuration as shown in FIG. 5, to a "stretched" configuration similar to that shown in FIG. 7. In the stretched configuration of FIG. 7, the disks are stretched by the opener 50 in the direction of the radial center of the disk. The void in the radial center of the figure indicates the presence of the opener 50.

The opener 50 is preferably inserted until the first valve disk 26 of the valve system reaches the larger diameter portion 54, which acts as a stop to prevent further insertion of the opener 50. As shown in FIGS. 13-14, the flared section 64 extends from a central region of the larger diameter portion 54. The elasticity of the valve disks allows the radial inner edges 29 of the valve disks to close in around the flared section 64 of the curved portion 62 when the opener 50 is inserted until the first valve disk 26 reaches the larger diameter portion 54. This prevents the opener 50 from popping out from the valve system within the apparatus 10 which is a very common problem, due to, for example, blood within the valve system or a lubricant, such as silicon, on the valve disks, associated with prior art valve openers having a generally uniform diameter.

Once the opener 50 has penetrated the disks as shown, a wire guide 25 may be inserted through the central bore 68 of the opener 50 such that is extends axially all the way through apparatus 10. The curved portion 62 of the opener 50 serves to keep the opener 50 stationary within the valve system while advancing and retracting wire guides in and out of central bore 68. The opener 50 may then be withdrawn leaving the wire guide in position.

In one example, the radius of the curved portion 62 is between about 0.08 inch and about 0.22 inch. In this example, the distance from the distal end 60 to the highest point of the curved portion 62 (i.e., where the diameter is $d_2$) is between about 0.75 inch and about 1.0 inch, and the distance from the highest point of the curved portion 62 to the larger diameter portion 54 is between about 0.2 inch and about 0.3 inch. These measurements, however, are only provided as an example and it should be noted that the opener 50 can be designed to fit the particular parameters of the particular valve system it is intended to penetrate. The opener 50 may also be used with valve systems other than hemostatic valve systems. The opener may be formed from nylon, polyethylene, or any suitable polymer. In addition, the opener may be formed from stainless steel or any suitable metal.

As illustrated in FIG. 13, the larger diameter portion 54 may be formed integrally with the tubular body 51. Alternatively, as illustrated in FIG. 14, the larger diameter portion 54 may be an annular ring 54 formed separately from the tubular body 51, in which case an opening 70 of the annular ring 54 includes an inner diameter $d_4$ larger than the outer diameter $d_3$ of the handle 56 and smaller than the outer diameter $d_5$ of the flared section 64. In this embodiment, the annular ring 54 slides over the handle 56 until it meets the flared section 64.

Figure 8:
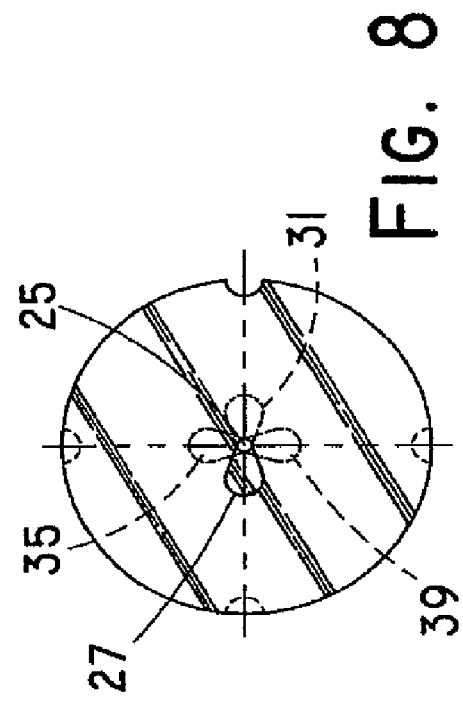
FIG. 8 illustrates the arrangement of disks shown in FIG. 5, following the insertion of a wire guide and the withdrawal of the opener.
Figure 9:
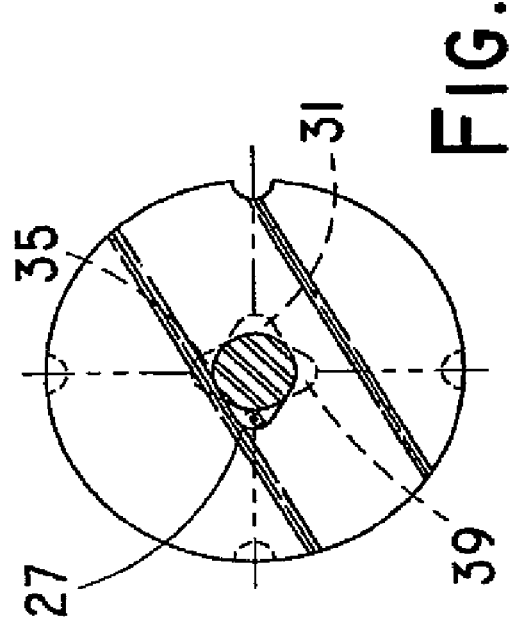
FIG. 9 illustrates the stretching pattern of the disks shown in FIG. 8, after an interventional device has been inserted into the valve system.
Figure 10:
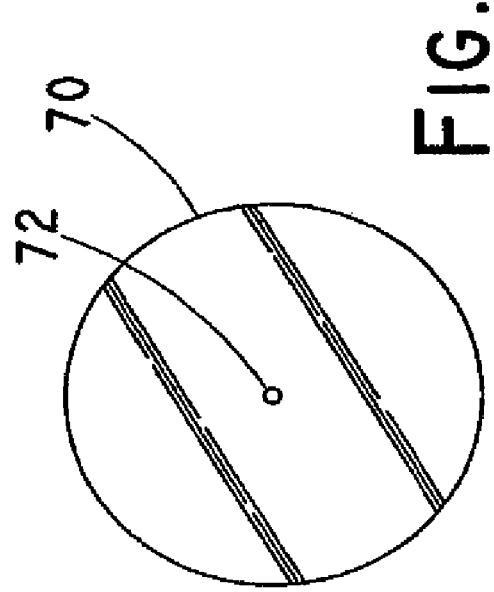
FIGS. 10 and 11 illustrate other stretching patterns of the disks shown in FIG. 8, after the insertion of respective larger interventional devices into the valve system.
Figure 11:
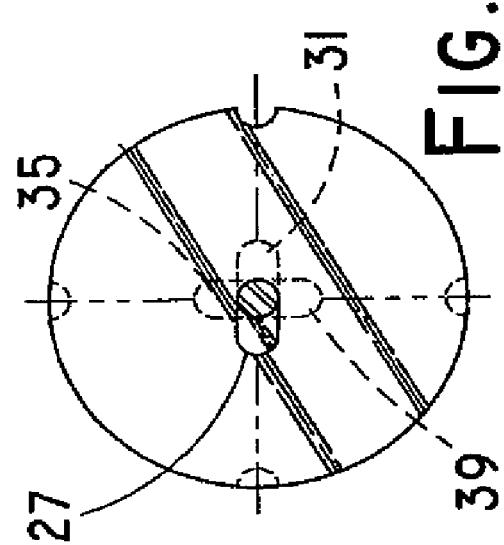

When the opener 50 has been removed and the wire guide 25 is left in position extending through apparatus 10, the holes have a stretched configuration such as that shown in FIG. 8. As shown, the radially inner edge of each successive hole 27, 31, 35, 39, is stretched toward the radial center of the apparatus. At this time, an interventional device, such as a catheter, may be inserted to follow the path through the introducer apparatus established by the wire guide. The hole in each of the elastomeric valve disks will automatically adjust to the dimensions of the inserted device. FIGS. 9, 10 and 11 illustrate examples of the type of stretching of the holes that may be caused by a relatively small diameter (FIG. 9), intermediate diameter (FIG. 10) and large diameter (FIG. 11) interventional device, respectively. In each case, as the tip of the catheter or other interventional device passes through the radial center of the valve system, it stretches the various loops (formed by stretching the respective holes), allowing the catheter to pass through the respective disk. At the same time, the curve of the loops hugs the outer surface of the catheter, thereby maintaining an effective seal therebetween. Once the catheter is removed, the elasticity of the disks causes them to revert to a condition wherein each successive disk covers the hole in an adjoining disk, as best shown in FIG. 5, thereby maintaining the seal.

Disks suitable for use in the present invention may be readily prepared in a manner generally similar to the preparation of existing hemostatic valve disks. In this case, however, rather than forming a slit and/or a central hole through the disk, a hole is punched or otherwise formed through the disk offset from the radial center. Since it is preferred to use disks that are identical to each other (differing only in their alignment in the valve system), a plurality of elastomeric disks may be simply arranged in a stack, and a hole punched through the stack. Similarly, if a notched portion is desired, the notched portion may also be punched into the stacked disks in a single operation. Those skilled in the art will appreciate that the holes and notched portions may alternatively be formed in the disks by any other conventional method, and all disks need not necessarily have the same orientation with regard to the offset hole and/or notched portion. However, utilizing a plurality of identical disks as described facilitates manufacture of the system.

Although the disks described above include notched portions that serve as "keys" for providing easy alignment of the disks in the housing, any other configuration that is capable of accomplishing the same purpose may be substituted. For example, a flattened portion can be provided along the circumference of the disks, or a slot can simply be cut through the edge of a designated portion of the disk. The housing can be formed to include complementary structure to receive the flattened portion or the slot, once again in the nature of a key. Those skilled in the art will appreciate that other complementary structures may be substituted for those described. Similarly, some disks may be provided with one type of key, such as a notch, while other disks can be provided with another type of key, such as a flattened portion. As still another alternative, the housing can be formed to have any other type of receptacle, tab, or guide that serves to maintain a disk in a constant orientation relative to other disks.

As yet another alternative, it is not required that the disks, or the housing, include a keyed portion at all. In some instances, merely stacking the disks in the housing in a manner similar to that of FIG. 5, wherein each successive disk substantially covers the hole of a preceding disk, will be sufficient. This will generally be true when only a low pressure rating of the valve disks is required.

Figure 12:
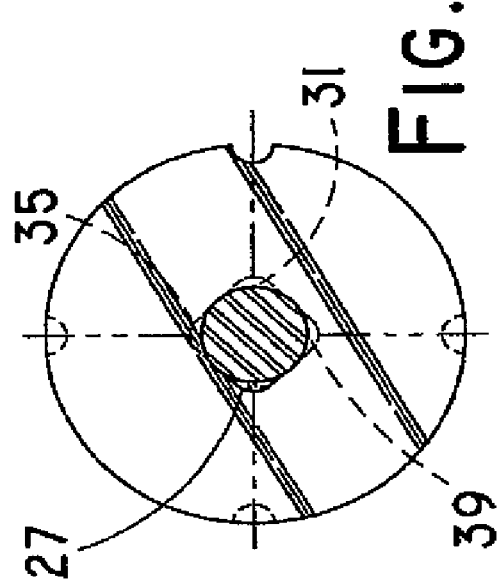
FIG. 12 is an example of a guide disk that may be utilized in connection with the inventive valve system.

As still another alternative, the valve system of the introducer apparatus can additionally include one or more additional disks not having the described configuration, and/or not covering the hole of a preceding disk. In one such embodiment, an additional disk can be provided in the housing body directly proximal of the disks of the described valve system. One such disk 70 is illustrated in FIG. 12. As shown, this disk includes a hole 72 through the radial center of the disk. Although the disk shown in FIG. 12 does not include a notch or other keyed portion, such portion(s) can be included if desired. This additional disk having a central hole may be particularly helpful in configurations where the holes in the aligned disks share a common point, such that the opener or wire guide may travel through the valve system substantially in a straight line. This disk is generally provided to guide the opener or wire guide through the system. As a result, this guide disk (or guide valve) may be arranged in the valve system such that it is the first disk encountered by the wire or device as it enters the proximal end of the introducer apparatus.

Utilizing disks having the offset holes as described for sealing is advantageous when compared to slitted valves. It is generally beneficial to utilize a curved line rather than straight lines in a passage or opening for an interventional device. A curved line has a better ability to "hug" the outer surface of the interventional device than a straight line, and thereby provides a better seal. In addition, the risk of tearing the disk is reduced, due to the larger opening that is possible with a hole when compared to a slitted opening. As a result, less force is required to close possible gaps in the valve system, and the insertion of larger devices is facilitated. Taking advantage of the stretching ability of the elastomeric disks provides the versatility to handle interventional devices having a wide range of diameters, and allows rapid recovery to the closed condition following passage therethrough of the device. Concern about the proper re-seating of the flaps of a V-shaped slitted opening following passage of the device is generally eliminated.

In addition to the foregoing, the stretching ability of the disks enables the sequential introduction and removal of interventional devices of a wide range of diameters through the same valve system. Thus, for example, a small catheter can be introduced and thereafter withdrawn, followed by the introduction of a larger catheter. In either case, the combination of the elasticity of the disks and the use of the circular offset openings provides a very reliable seal. Similarly, with a circular hole, the pressure is distributed in a substantially equal manner around the entire outer circumference of the interventional device. As a result, less pressure is exerted against localized portions of the surface of the interventional device. This is particularly advantageous for the insertion of delicate and/or very small diameter devices, which may be at risk of collapse if excessive pressure is exerted on the device during introduction. Depending upon the composition of the disk, a hole may stretch up to about five times its normal size.

Those skilled in the art will appreciate that lubricants and other conventional additives for use with conventional check flow valves may also be utilized with the valves of the present invention. In particular, the use of lubricants between the disks may be desired to inhibit stickage of adjacent disks, and to assist in the smooth movement of the interventional device through the holes.

It is therefore intended that the foregoing detailed description be regarded as illustrative rather than limiting, and that it be understood that it is the following claims, including all equivalents, that are intended to define the spirit and scope of this invention.

The invention claimed is:

1. A valve opener for insertion through a valve system having a plurality of axially arranged valve members, each valve member including a generally circular hole extending therethrough, the valve opener comprising:
   a tubular body including proximal and distal ends and a central bore formed through the proximal and distal ends defining a longitudinal axis, the tubular body including a handle portion extending from the proximal end to a larger diameter portion and a distal portion extending from the larger diameter portion to the distal end, the distal portion having a flared section extending from the larger diameter portion and a tapered section extending from the flared section, wherein the larger diameter portion has a first outer diameter larger than a second outer diameter of the distal portion, the second outer diameter of the distal portion being the greatest outer diameter of the distal portion, wherein the flared section has a third outer diameter increasing distally along the longitudinal axis and the tapered section has a fourth outer diameter decreasing distally along the longitudinal axis to the distal end, the fourth outer diameter of the tapered section continuously decreasing from the second outer diameter to the distal end.

2. The valve opener of claim 1 wherein the distal end sequentially penetrates each of the generally circular holes of the valve members when the valve opener is advanced through the valve system.

3. The valve opener of claim 1 wherein the larger diameter portion acts as a stop when the valve opener is advanced through the valve system to prevent further insertion of the valve opener within the valve system.

4. The valve opener of claim 1, each valve member of the valve system having a radial inner edge about the hole, wherein the valve opener engages the radial inner edge of a first valve member and is continually advanced until it reaches the radial inner edge of each successive valve member, wherein the valve opener is manipulated to stretch the holes in an up and down, and in a side to side motion to establish a path for an interventional device.

5. The valve opener of claim 1, each valve member of the valve system having a radial inner edge about the hole, wherein the valve opener is advanced through the valve system until the larger diameter portion abuts a first valve member, wherein the radial inner edge of at least the first valve member closes in around the flared section of the valve opener and prevents the valve opener from proximally popping out from within the valve system.

6. The valve opener of claim 1 wherein the flared section extends from a central region of the larger diameter portion.

7. The valve opener of claim 1 wherein the flared section and the tapered section define a curved portion which maintains the valve opener stationary within the valve system during insertion and removal of a wire member through the central bore of the valve opener.

8. The valve opener of claim 1 wherein the larger diameter portion is formed integrally with the tubular body.

9. The valve opener of claim 1 wherein the larger diameter portion is an annular ring formed separately from the tubular body and includes an opening having an inner diameter larger than a fifth outer diameter of the handle portion and smaller than the third outer diameter of the flared section, wherein the annular ring slides over the handle portion until it meets the flared section.

10. The valve opener of claim 1 wherein the valve opener is sized according to the number of valve members within the valve system, such that when the valve opener is fully inserted within the valve system at least a first valve member engages with the flared section and at least a second valve member engages with the tapered section.

11. A hemostatic valve system for use in a medical introducer, the valve system comprising:
   a plurality of valve members having a hole extending therethrough, the valve members axially arranged in the medical introducer, the holes having a diameter that does not substantially exceed a diameter of an interventional device to be passed through the medical introducer and the valve members, the valve members being aligned in the medical introducer such that the holes are penetrable by the interventional device, and such that a hole in one valve member is covered by an adjoining valve member; and
   a valve opener configured to advance through the plurality of valve members to establish a pathway through the valve members for insertion of the interventional device, the valve opener including a tubular body including proximal and distal ends and a central bore formed through the proximal and distal ends defining a longitudinal axis, the tubular body including a handle portion extending from the proximal end to a larger diameter portion and a distal portion extending from the larger diameter portion to the distal end, the distal portion having a flared section extending from the larger diameter portion and a tapered section extending from the flared section, wherein the larger diameter portion has a first outer diameter larger than a second outer diameter of the distal portion, the second outer diameter of the distal portion being the greatest outer diameter of the distal portion, wherein the flared section has a third outer diameter increasing distally along the longitudinal axis and the tapered section has a fourth outer diameter decreasing distally along the longitudinal axis to the distal end, the fourth outer diameter of the tapered section continuously decreasing from the second outer diameter to the distal end.

12. The valve system of claim 11 wherein the distal end of the valve opener sequentially penetrates each of the holes of the valve members when the valve opener is advanced through the valve system.

13. The valve opener of claim 11 wherein the larger diameter portion acts as a stop when the valve opener is advanced through the valve system to prevent further insertion of the valve opener within the valve system.

14. The valve system of claim 11, each valve member of the valve system having a radial inner edge about the hole, wherein the valve opener engages the radial inner edge of a first valve member and is continually advanced until it reaches the radial inner edge of each successive valve member, wherein the valve opener is manipulated to stretch the holes in an up and down, and in a side to side motion to establish a path for an interventional device.

15. The valve system of claim 11, each valve member of the valve system having a radial inner edge about the hole, wherein the valve opener is advanced through the valve system until the larger diameter portion abuts a first valve member, wherein the radial inner edge of at least the first valve member closes in around the flared section of the valve opener and prevents the valve opener from proximally popping out from within the valve system.

16. The valve system of claim 11 wherein the flared section and the tapered section define a curved portion which maintains the valve opener stationary within the valve system during insertion and removal of a wire member through the central bore of the valve opener.

17. The valve system of claim 11 wherein the larger diameter portion of the valve opener is an annular ring formed separately from the tubular body and includes an opening having an inner diameter larger than a fifth outer diameter of the handle portion of the valve opener and smaller than the third outer diameter of the flared section of the valve opener, wherein the annular ring slides over the handle portion until it meets the flared section.

18. The valve system of claim 11 wherein the plurality of valve members is axially arranged in the medical introducer such that the holes are substantially non-coaxial and are offset from a center portion of the valve, the holes further being capable of substantially conforming to the profile of the interventional device as the interventional device is passed through the path established by the valve opener after removal of the valve opener from the valve system.

19. The valve system of claim 11 wherein the valve opener is sized according to the number of valve members within the valve system, such that when the valve opener is fully inserted within the valve system at least a first valve member engages with the flared section and at least a second valve member engages with the tapered section.

* * * * *